United States Patent
Al Najjar et al.

(10) Patent No.: US 10,449,677 B1
(45) Date of Patent: Oct. 22, 2019

(54) ROBOTIC GRIPPING ASSIST

(71) Applicant: UNITED ARAB EMIRATES UNIVERSITY, Al Ain (AE)

(72) Inventors: Fady Al Najjar, Al Ain (AE); Nouf Fadel Nasser Alsaedi, Al Ain (AE); Waleed Khalil Ahmed, Al Ain (AE)

(73) Assignee: United Arab Emirates University, Al-Ain (AE)

( * ) Notice: Subject to any disclaimer, the term of this patent is extended or adjusted under 35 U.S.C. 154(b) by 0 days.

(21) Appl. No.: 16/351,458

(22) Filed: Mar. 12, 2019

(51) Int. Cl.
| | | |
|---|---|---|
| *A61H 1/02* | (2006.01) | |
| *B25J 15/00* | (2006.01) | |
| *B25J 13/08* | (2006.01) | |
| *A41D 19/01* | (2006.01) | |

(52) U.S. Cl.
CPC .......... *B25J 15/0009* (2013.01); *A41D 19/01* (2013.01); *A61H 1/0288* (2013.01); *B25J 13/085* (2013.01); *A41D 2400/32* (2013.01); *A61H 2201/165* (2013.01); *A61H 2201/1638* (2013.01); *A61H 2201/1659* (2013.01); *A61H 2201/5071* (2013.01)

(58) Field of Classification Search
CPC .. A61H 1/0285; A61H 1/0274; A61H 1/0288; A61H 1/02; A61B 5/0022; A61B 5/225; A61B 5/6806; A63B 23/035; A63B 23/00; A63B 21/4019; A63B 21/4035; G06F 3/014
See application file for complete search history.

(56) References Cited

U.S. PATENT DOCUMENTS

| | | | | | |
|---|---|---|---|---|---|
| 5,178,137 | A | * | 1/1993 | Goor | A61F 5/0111 601/40 |
| 5,516,249 | A | * | 5/1996 | Brimhall | B25J 3/04 414/5 |
| 5,697,892 | A | * | 12/1997 | Torgerson | A61H 1/0288 601/40 |
| 5,945,978 | A | * | 8/1999 | Holmes | G06F 3/014 345/156 |

(Continued)

FOREIGN PATENT DOCUMENTS

| | | |
|---|---|---|
| CN | 102941579 A | 2/2013 |
| CN | 206393633 U | 8/2017 |

(Continued)

OTHER PUBLICATIONS

Resna14y80sdc "Exoarm" RESNA, RERC on AAC and NSF, Apr. 20, 2014.

*Primary Examiner* — Alvin J Stewart
(74) *Attorney, Agent, or Firm* — Richard C. Litman; Nath, Goldberg & Meyer

(57) ABSTRACT

The robotic gripping assist ("RGA") provides a user with additional grip strength by supporting and forcefully pushing a user's fingers and hand to a gripping position. A motor, controller, and power source are supported on a user's forearm and act as a source for the forced movement. A bending member is worn on the back of a user's hand. The motor draws in or lets out wires that cause the bending member to bend or straighten. By bending the bending member, through rotating the motor in a first direction, the attached fingers of the user are forced into a gripping position. The fingers are moved to a non-gripping position by rotating the motor in the opposite direction.

10 Claims, 15 Drawing Sheets

(56) References Cited

U.S. PATENT DOCUMENTS

| | | | |
|---|---|---|---|
| 6,896,704 B1* | 5/2005 | Higuchi | A61F 2/583 623/25 |
| 7,862,522 B1* | 1/2011 | Barclay | G06F 3/014 414/2 |
| 8,029,414 B2* | 10/2011 | Ingvast | A61H 1/0288 482/47 |
| 8,622,939 B2* | 1/2014 | Nguyen | A61H 1/0288 482/44 |
| 8,849,453 B2* | 9/2014 | Bergelin | B25J 9/0006 700/250 |
| 8,998,831 B2* | 4/2015 | Sankai | A61B 5/04888 601/40 |
| 9,067,325 B2* | 6/2015 | Ihrke | B25J 15/08 |
| 9,120,220 B2* | 9/2015 | Bergelin | B25J 9/0006 |
| 9,149,933 B2* | 10/2015 | Ihrke | B25J 9/104 |
| 9,375,382 B2* | 6/2016 | Fausti | A61H 1/0285 |
| 9,532,916 B2* | 1/2017 | Tsui | A61H 1/0285 |
| 10,248,200 B2* | 4/2019 | Cohen | B25J 13/025 |
| 2003/0195093 A1* | 10/2003 | White | A63B 21/0552 482/124 |
| 2006/0094989 A1* | 5/2006 | Scott | A61F 2/54 601/5 |
| 2010/0305717 A1* | 12/2010 | Tong | A61H 1/0285 623/64 |
| 2012/0065026 A1* | 3/2012 | Land | A63B 21/00065 482/47 |
| 2013/0072829 A1* | 3/2013 | Fausti | A61H 1/0285 601/40 |
| 2013/0226350 A1* | 8/2013 | Bergelin | B25J 9/0006 700/275 |
| 2013/0261514 A1* | 10/2013 | Tsui | A61H 1/0285 601/40 |
| 2016/0193101 A1* | 7/2016 | Pu | A61F 2/70 623/24 |
| 2017/0042704 A1* | 2/2017 | Ryu | A61F 2/583 |
| 2017/0071272 A1* | 3/2017 | Carey | A41D 19/01582 |
| 2017/0119614 A1* | 5/2017 | Yeow | A61H 1/0266 |
| 2017/0168565 A1* | 6/2017 | Cohen | B25J 13/025 |
| 2017/0266075 A1* | 9/2017 | Becchi | A61H 1/0288 |
| 2018/0125692 A1 | 5/2018 | Takenaka et al. | |
| 2018/0296419 A1* | 10/2018 | Tong | A61H 1/02 |
| 2018/0303698 A1* | 10/2018 | Wijesundara | F15B 15/10 |
| 2018/0311570 A1* | 11/2018 | Buchanan | A63F 13/42 |
| 2018/0335842 A1* | 11/2018 | Rubin | G06F 3/014 |
| 2018/0345481 A1* | 12/2018 | Cho | B25J 9/104 |
| 2019/0056248 A1* | 2/2019 | Shepherd | G01B 11/16 |
| 2019/0152049 A1* | 5/2019 | Luijten | A61B 5/225 |

FOREIGN PATENT DOCUMENTS

| | | |
|---|---|---|
| JP | 2016129916 A | 7/2016 |
| WO | 2017133131 A1 | 8/2017 |

\* cited by examiner

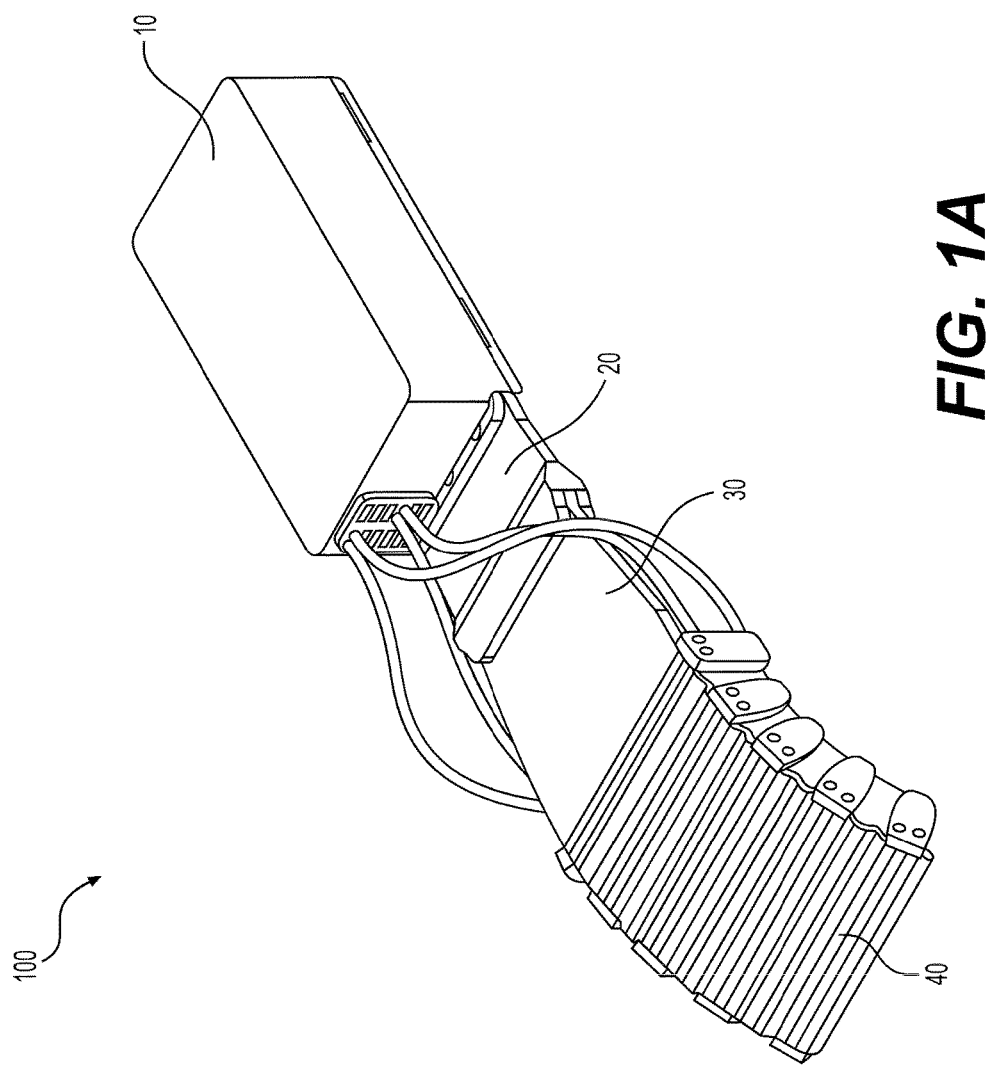

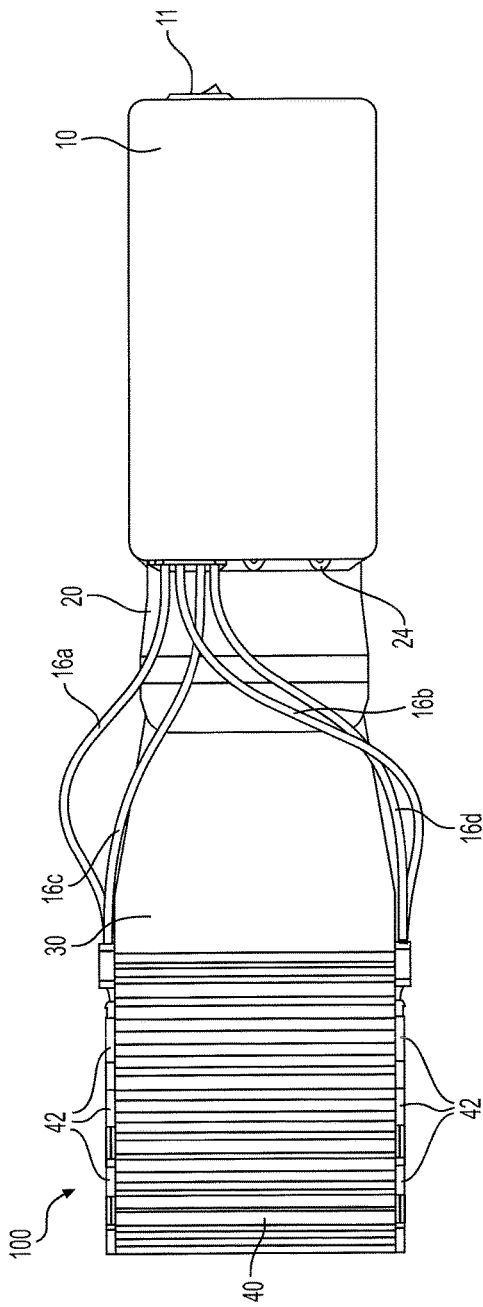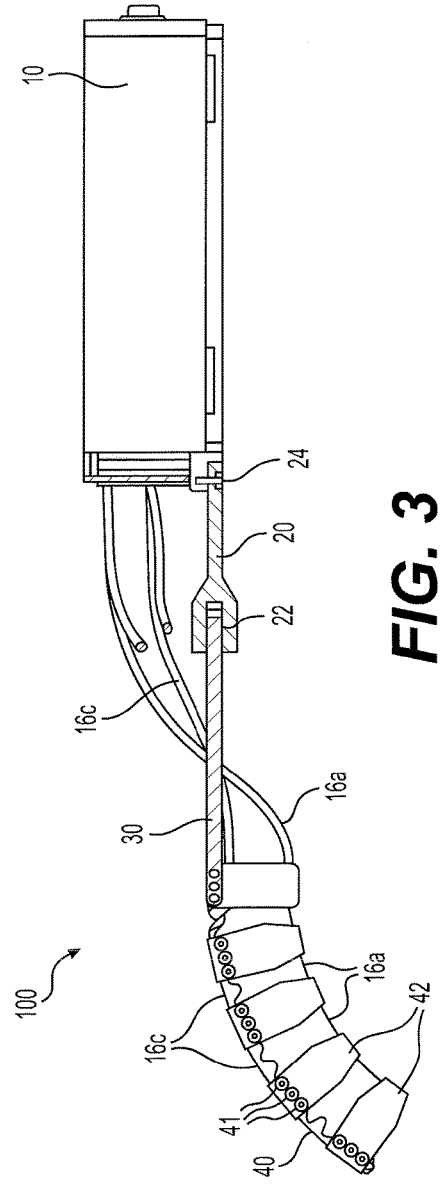
FIG. 2
FIG. 3

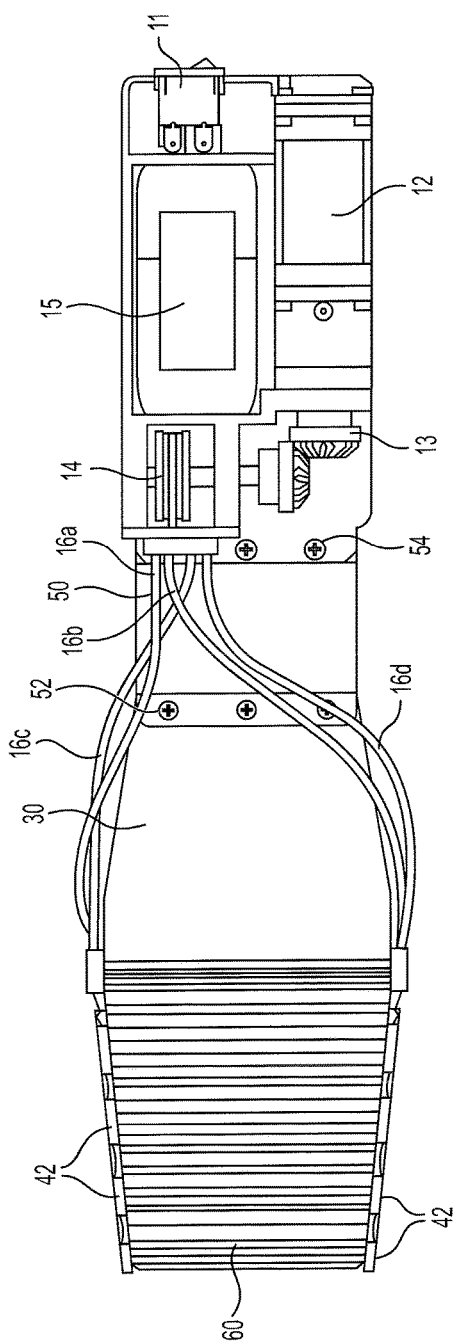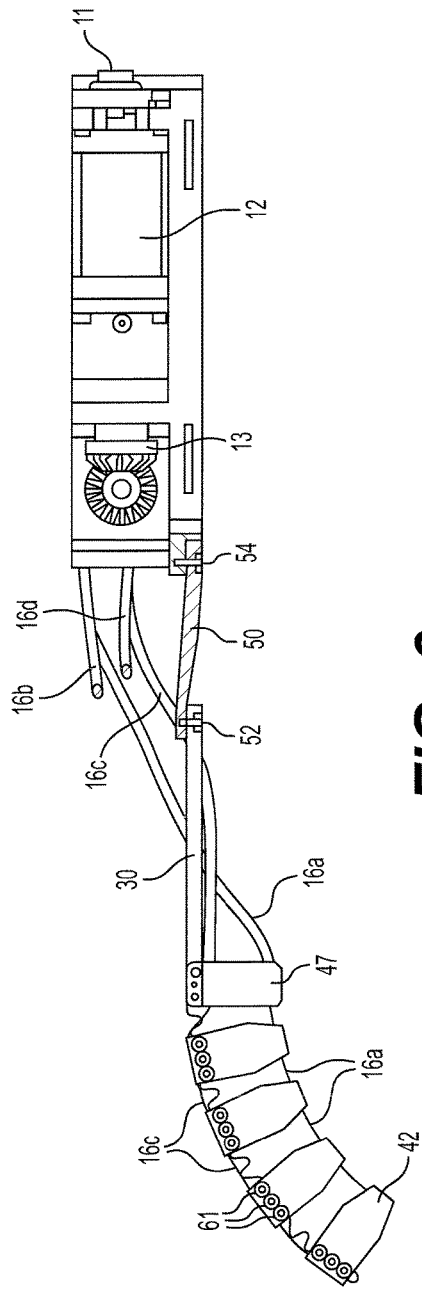
FIG. 5
FIG. 6

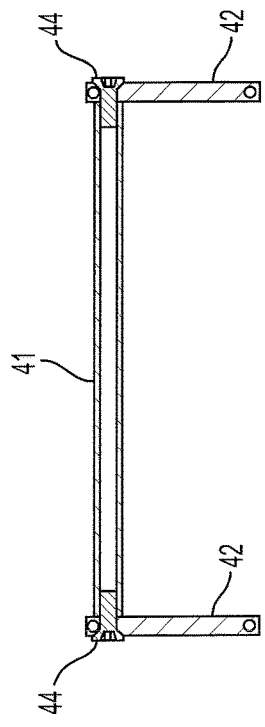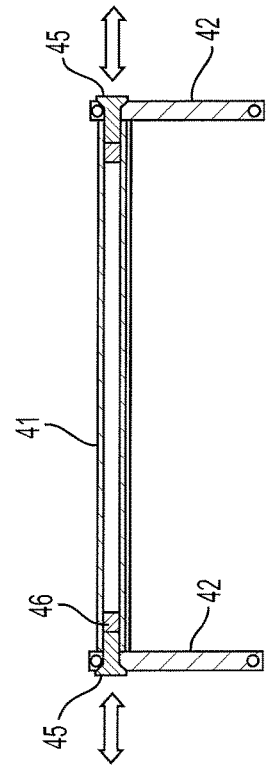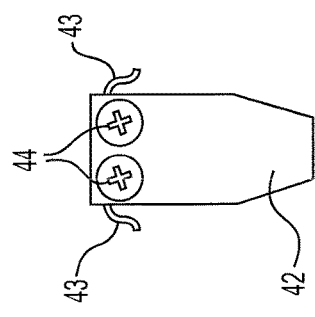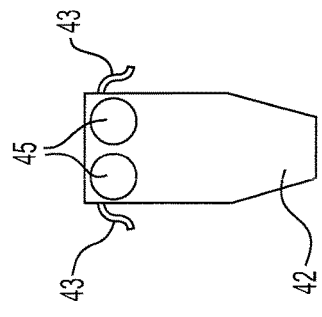
FIG. 9B
FIG. 9D
FIG. 9A
FIG. 9C

ROBOTIC GRIPPING ASSIST

BACKGROUND

1. Field

The disclosure of the present patent application relates to robotic human assistance, and particularly to a robotic gripping assist that may be worn on the lower arm and hand to provide additional grip strength for persons that have lost grip strength due to stroke and other neuromuscular impairments.

2. Description of the Related Art

Robotics includes several different research areas, procedures, and clinical and automatic programs, as well as those fields dealing with disability assistance. Applications of support robotics have focused on healing or improving physical afflictions, such as helping patients execute repeated healing actions. Robotic recovery apparatuses have the following advantages: high competence; restorative therapy; robot-supported exercises can be executed without assistance; precise outputs; and shortened recovery.

Research has shown that stroke patients who have been assisted by robots when executing repeated activities present a significant improvement in hand action performance. Furthermore, the use of robotics allows therapists to be relieved from time-consuming exercise tasks. Moreover, patients' rehabilitation situations can be easily evaluated using information recorded through the robotic exercise progress. Finally, wearable hand robotics can effectively enhance rehabilitation output after a stroke.

The hand is the primary part of the body that interacts with objects. Humans are capable of more precise hand actions than other creatures through a highly complex sensorimotor structure utilizing optical data and the physical hand mechanism (hand-eye coordination). People who have suffered a stroke display different disabilities and problems performing daily activities. New recovery procedures utilizing robot recovery devices are gaining the attention of researchers, programmers, and doctors. The primary aim of producing wearable hand robotics is to develop a device that facilitates patient recovery.

However, wearable robotic support arms have both hardware and software limitations. One major software obstacle occurs when the robot does not efficiently define and interact with the activities and purposes of the wearer. For example, the robot must be fit for use at home so patients can execute treatments on their own.

Thus, a robotic gripping assist solving the aforementioned problems is desired.

SUMMARY

The robotic gripping assist ("RGA") provides a user with additional grip strength by supporting and forcefully pushing a user's fingers and hand to a gripping position. A motor, controller, and power source are supported on a user's forearm and act as a source for the forced movement. A bending member is worn on the back of a user's hand. The motor draws in or lets out wires that cause the bending member to bend or straighten. By bending the bending member, through rotating the motor in a first direction, the attached fingers of the user are forced into a gripping position. The fingers are moved to a non-gripping position by rotating the motor in the opposite direction.

The RGA is attached to the user's hand and arm using a mitten and arm wrap that connected directly to the RGA. Straps that wrap around the mitten and arm wrap are also used for securement. Once the device is secured to the user, the user can function normally with the benefit of added grip strength.

These and other features of the present disclosure will become readily apparent upon further review of the following specification and drawings.

BRIEF DESCRIPTION OF THE DRAWINGS

FIG. 1A is a perspective view of a first embodiment of a robotic gripping assist.

FIG. 2 is a top view of the robotic gripping assist of FIG. 1.

FIG. 3 is a side view of the robotic gripping assist of FIG. 1, shown with some components of the bending member in section.

FIG. 5 is a top view of robotic gripping assist of FIG. 4, shown with the protective cover removed from the arm box.

FIG. 6 is a side view of the robotic gripping assist of FIG. 4, shown with the protective cover removed from the arm box and with some components of the bending member in section.

FIG. 9A is a diagrammatic side view of a support member attached to the bending member according to a first embodiment of an attachment mechanism.

FIG. 9B is a side view in section taken through a rigid rod and opposing support members attached to the bending member according to the attachment method of FIG. 9A.

FIG. 9C is a diagrammatic side view of a support member attached to the bending member according to a second embodiment of an attachment mechanism.

FIG. 9D is a side view in section taken through a rigid rod and opposing support members attached to the bending member according to the attachment method of FIG. 9C.

Similar reference characters denote corresponding features consistently throughout the attached drawings.

DETAILED DESCRIPTION OF THE PREFERRED EMBODIMENTS

The robotic gripping assist ("RGA") provides a user with additional grip strength by supporting and forcefully pushing a user's fingers and hand to a gripping position. A motor, controller, and power source are supported on a user's forearm and act as a source for the forced movement. A bending member is worn on the back of a user's hand. The motor draws in or lets out wires that cause the bending member to bend or straighten. By bending the bending member, through rotating the motor in a first direction, the attached fingers of the user are forced into a gripping position. The fingers are moved to a non-gripping position by rotating the motor in the opposite direction.

Figure 1B:
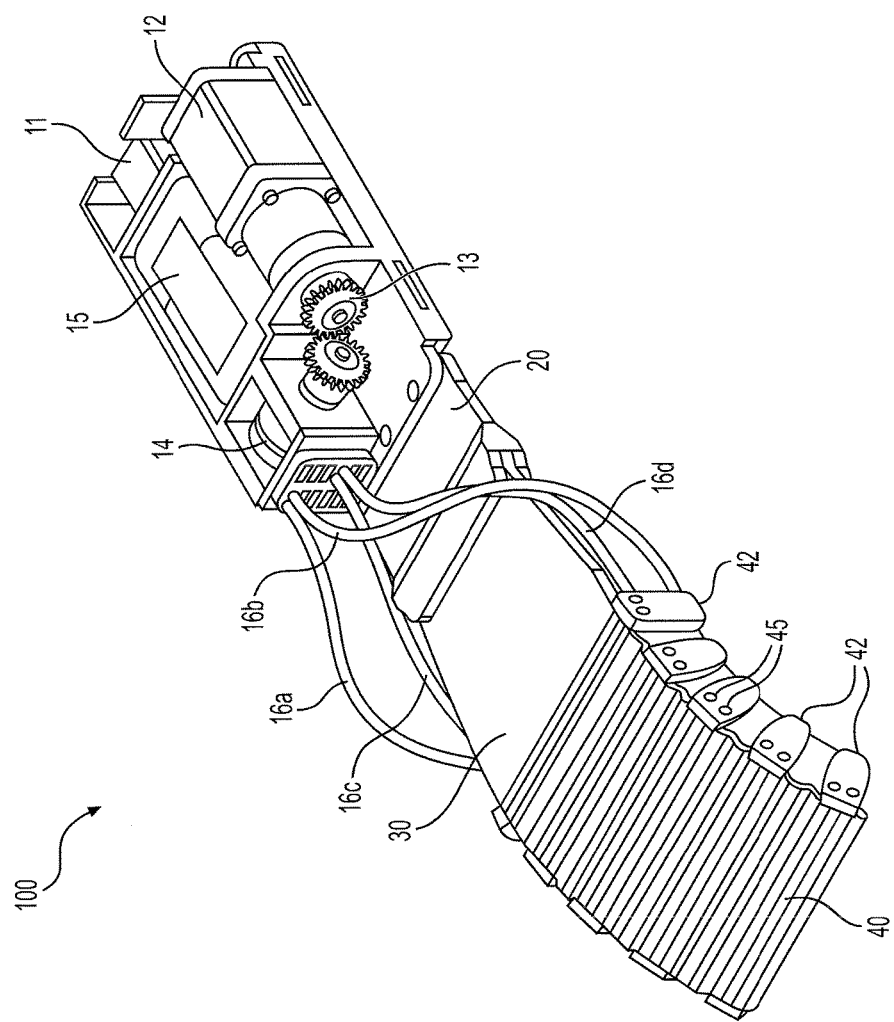
FIG. 1B is a perspective view of the robotic gripping assist of FIG. 1, shown with the protective cover removed from the arm box.

FIG. 1A shows a first embodiment of the RGA 100. The RGA 100 includes an arm box 10 connected to a base member 20, which is attached to a bending member 40 through an intermediate member 30. As seen in FIG. 1B, which shows the arm box 10 without its cover, the arm box 10 houses a power switch 11, a motor 12, a gear train 13, a spool 14, and a battery 15. Four wires 16a, 16b, 16c, and 16d are strung through support elements 42 attached to the sides of the bending member 40 along its length.

FIGS. 2 and 3 are top and side views, respectively, of the RGA 100. FIG. 2 shows the bending member 40 is a corrugated, flexible belt having a rectangular shape (i.e., substantially uniform width) with support members 42 attached to opposing sides. As seen in FIG. 3, the tops of the support members 42 are connected to the bending member 40 and may be evenly spaced along its length. Two of the wires 16a, 16b are strung through the bottom of the support elements 42, one on each side of the bending member 40, and the other two wires 16c, 16d are strung through the top of the support members 42, with one on each side of the bending member 40. Since the tops of the support elements 42 are spaced apart, pulling on the bottom wires approximates only the bottoms of the support members 42. The approximation of the support member bottoms, while the tops of the support members 42 remain separated by the bending member 40 causes the bending member 40 to bend downward, as seen in FIG. 3. The bottoms of the support members 42 may be tapered inwards to allow for greater downward bend of the bending member 40 due to a greater range of approximation. While the lower wires 16a, 16b are pulled in, the upper wires 16c, 16d are let out to allow the bending member 40, which is located at the top of the support member 42, to bend downward. A proximal-most (proximal to the intermediate member 30) support member 42 may be connected to the intermediate member 30 to provide a first rigid support, towards which the other support members 42 will be pulled.

The base member 20 provides a rigid connection between the intermediate member 30 and the arm box 10. In the embodiment of FIGS. 1-3, the base member 20 has a planar proximal portion (proximal to the arm box 10), which is bolted to the arm box 10 by bolts 24, and a distal portion defining a channel 22. The channel 22 is dimensioned and configured to receive the proximal end of the intermediate member 30. The intermediate member 30 may be secured in the channel 22 by magnets to allow for quick assembly and disassembly. Since the forces of the intermediate member 30 acting on the base member 20 will primarily be rotational, the magnetic connection is adequate for securing the joint during operation. The intermediate member 20 may be dimensioned based on the user's hand size. Accordingly, a user with a large hand may use a device having a large intermediate member 20, and a user with a small hand may use a device with a small intermediate 20 member. In some embodiments, the intermediate member 20 may be interchangeable with intermediate members of different length so that the RGA 100 can accommodate users with different hand sizes.

Figure 4:
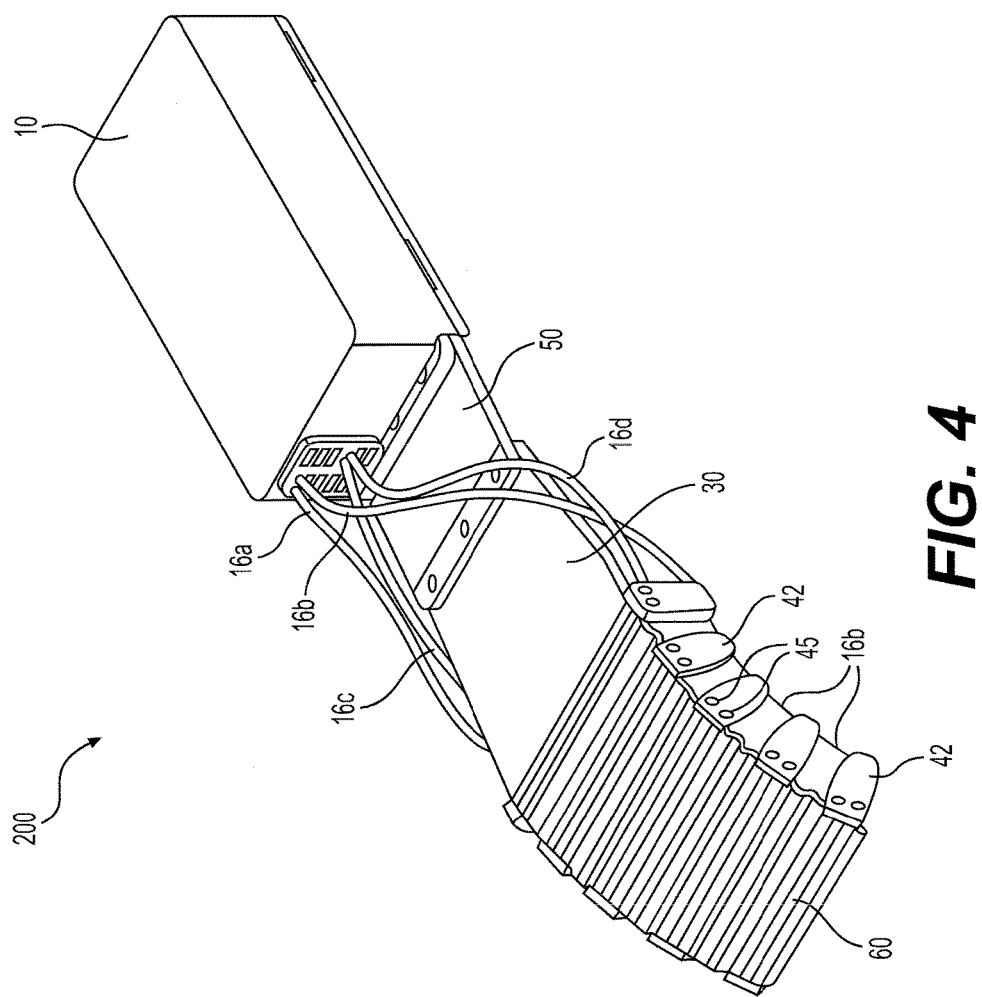
FIG. 4 is a perspective view of a second embodiment of the robotic gripping assist.

A second embodiment of the RGA 200 is shown in FIGS. 4-6. The primary difference between the first and second embodiments is the shape of the bending member 60. The RGA 100 of FIGS. 1-3 has a rectangular shaped bending member 40 while the RGA 200 of FIGS. 4-6 has a bending member 60 that tapers in width inward towards its distal end. As best seen in FIG. 5, the bending member 60 tapers inwards towards its distal end to produce an end portion with a smaller width. This embodiment may be used for situations where there is not enough room to efficiently operate the embodiment having a full width end. The base member 50 is also different than the base member 20 of the first embodiment. In this embodiment, the base member 50 is similarly bolted to the bottom of the arm box 10, but does not have a channel 22 at the opposing end. Instead, the base member 50 bolts to the top of the intermediate member 30, as shown in FIG. 6. This embodiment may allow for more flexibility in the intermediate member/base member section of the device. Either base member 20, 50 may be used with either bending member 40, 60.

FIGS. 5 and 6 show the arm box 10 with the protective cover removed. A back of the housing of the arm box 10 may hold a power switch 11 configured to be operated by a user. The switch 11 is connected to the motor 12, which may include an integrated motor controller. The output shaft of the motor 12 may be connected to a gear train 13 that changes the axis of rotation 90° to align the wire spool 14 with the bending member 60. As previously discussed, four wires 16a-16d are wrapped around the spool 14, with the two upper wires 16a, 16b wrapped in one direction and the two lower wires 16c, 16d wrapped in the opposite direction. Similar to the previous embodiment, the two upper wires 16a, 16b are strung through the top of the support members on opposing sides of the bending member 60 and the two lower wires 16c, 16d are strung through the bottoms of the support members 42 on opposing sides of the bending member 50. Since the wires 16a-16d are wrapped around the spool 14 in opposite directions, rotating the spool 14 will let the wires wrapped in one direction out and will simultaneously pull the wires wrapped in the other direction in. In some cases, the lower wires 16a, 16b will require more movement than the upper wires 16c, 16d. In these cases, the lower wires 16*a*, 16*b* can be wrapped around a larger spool and the upper wires 16*c*, 16*d* can be wrapped around a smaller spool.

Figure 7:
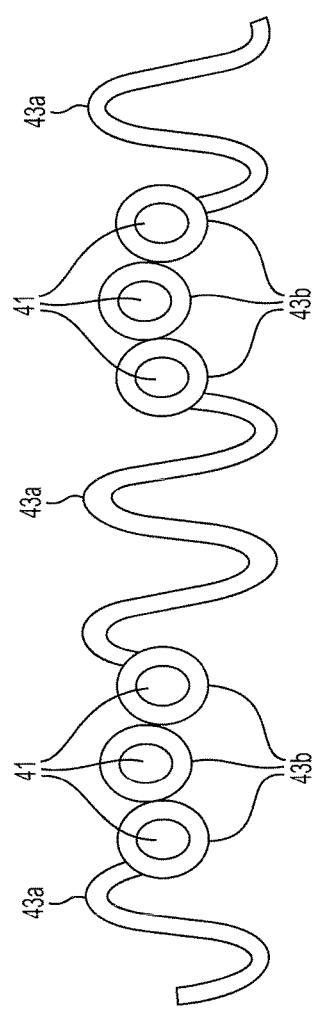
FIG. 7 is a diagrammatic side view of the bending member.
Figures 8A, 8B, 8C, 8D:
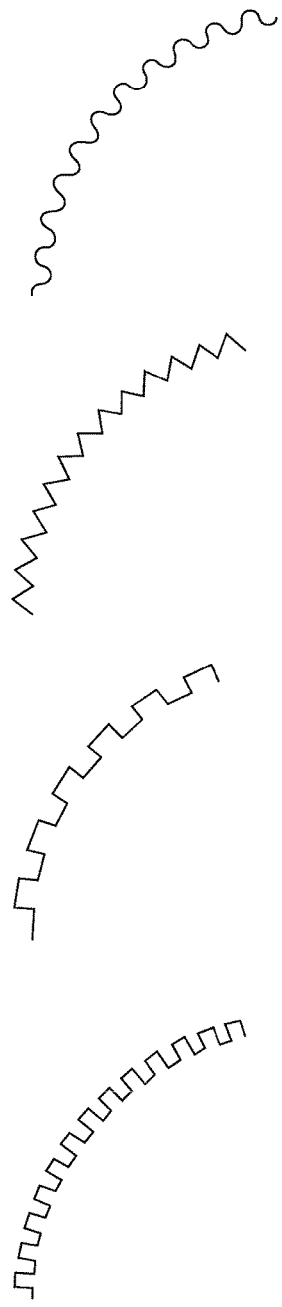
FIGS. 8A, 8B, 8C, and 8D are diagrammatic side views of alternative configurations of the wave portions of the bending member.

FIG. 7 shows a diagrammatic side view of an embodiment of the bending member 40. The bending member 40 includes rigid rods or members 41 and a flexible belt 43*a*. The flexible belt 43*a* includes wave portions and sheath portions 43*b* encasing the rigid members alternately along its length. The wave portions extending between groups of sheathed rigid members 41 are shown as being two wavelengths, but may include more or less wavelengths to increase or decrease flexibility. The sheath portions 43*b* may include three cylindrical sheaths connected along their length with the middle sheath offset from the sheaths on opposing sides. The rigid rods 41 are located in the sheaths 43*b* for providing rigidity to the bending member 40 so that it primarily bends along its length dimension and not along its width dimension.

FIG. 3 also shows a side view of the bending member 40. As seen in FIG. 3, the rigid rods 41 provide rigid attachment points for the support members 42. Accordingly, the bending forces from the support members 42 are evenly distributed along the width of the bending member 40 by the rigid rods 41. By alternating the flexible wave portions of the belt 43*a* and the sheath portions 43*b* containing the rigid rods 41, the corrugated bending member 40 is provided with the necessary flexibility along its length for moving from a straight to a gripping position, while having the stability to prevent bending in a width direction and evenly distributing the forces from the support members 42. In addition to flexing downward when moving from a straight to a gripping position, the bending member 40 also experiences compression and extension along its length. The multiple wavelength wave portions between the sheath portions 43*b* allow the bending member 40 to compress and extend during operation. FIGS. 8A-8D show different shapes and relative dimensions that may be used for the wave portions of the bending member 40, e.g., square wave (FIGS. 8A, 8B), sawtooth (FIG. 8C), sine wave (FIG. 8D), etc. Different shapes and relative dimensions of the wave portions change the flexion, compression, and extension characteristics of the bending member 40. The aforementioned structure may be used on tapered bending member 60, such as in the second embodiment FIGS. 9A-9B show a first method for connecting the support elements 42 to the bending member 40. As previously discussed with regard to FIG. 7, the bending member 40 includes sections contain three adjacent rigid rods 41. Each section of rods 41 may be connected to a support member 42 by two screws 44, one in each of the two outer rods 41. As seen in FIG. 9A-9B, two screws extend through holes in the upper portion of the support member 42 and into a threaded bore in the rods 41. FIGS. 9C-9D show a second method for connecting the support elements 42 to the bending member 40. In the second method, pins 45 are used in place of screws 44, and the pins 45 are held in place by a magnet 46 seated within the bore of the rods 41. This method may allow for quicker attachment and removal of the support member 42 since the pins 45 can be simply pilled out or pushed in. Alternatively, the pins 45 may be used for the proximal-most support member 42, and the screws may be used for the distal support members 42. This configuration will allow the bending member 40 to be easily removed from the intermediate member 30, while maintaining the security of screws 44 on the distal support members 42.

Figure 10B:
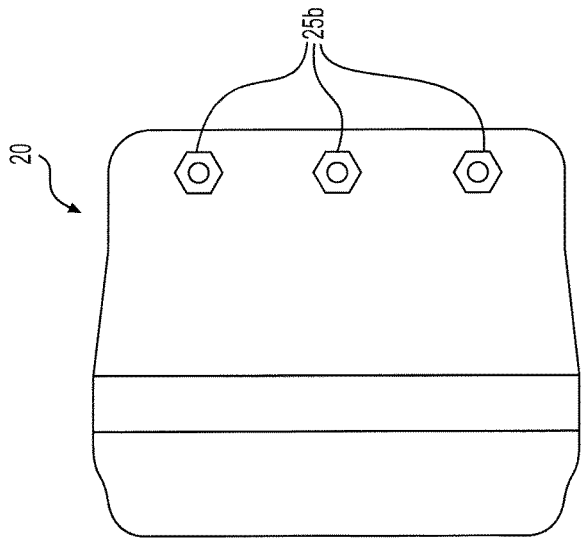
FIG. 10B is a bottom view of the base member of FIG. 10A.
Figure 10D:
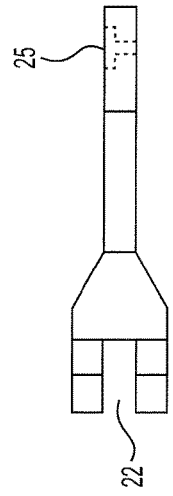
FIG. 10D is a side view of the base member of FIG. 10A.
Figure 10A:
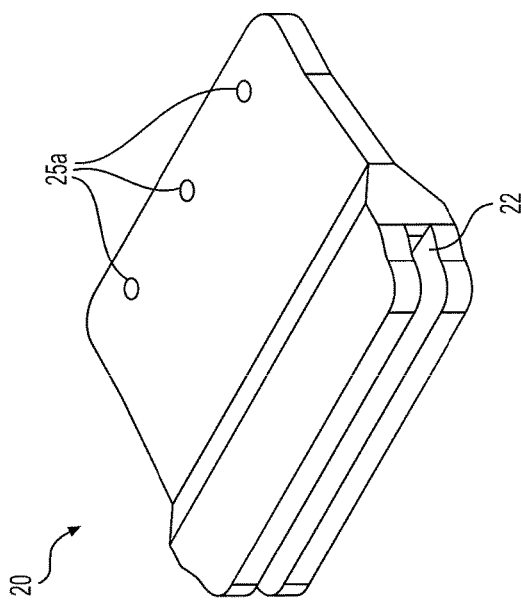
FIG. 10A is a perspective view of a first embodiment of the base member.
Figure 10C:
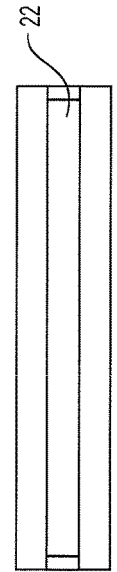
FIG. 10C is a front view of the base member of FIG. 10A.

FIGS. 10A-10D show details of the base 20 of FIGS. 1-3, which may use magnetic force to maintain a connection with the intermediate member 30. Similar to the previously mentioned magnetic pins 45, the magnetic connection allows for quick assembly and disassembly. As seen in FIGS. 10A and 10B, the proximal end of the base member 20 is a planar plate having holes 25*a* along its proximal edge for bolting to the arm box 10. As seen in FIGS. 10B and 10D, the holes 25*b* may have a countersink 25 to accept the bolt head 24 for maintaining a flat arm contacting surface. The distal end of the base member 20 defines a channel 22 running along its length for accepting the proximal end of intermediate member 30 (see FIG. 3). Magnets may be dispersed throughout the channel 22 portion for securing the intermediate member 30 once it is in place. As previously discussed, the primary forces of the intermediate member 30 on the base member 20 will be rotational. Therefore the structure of the channel 22, not the magnets, will counteract these forces.

Figure 11A:
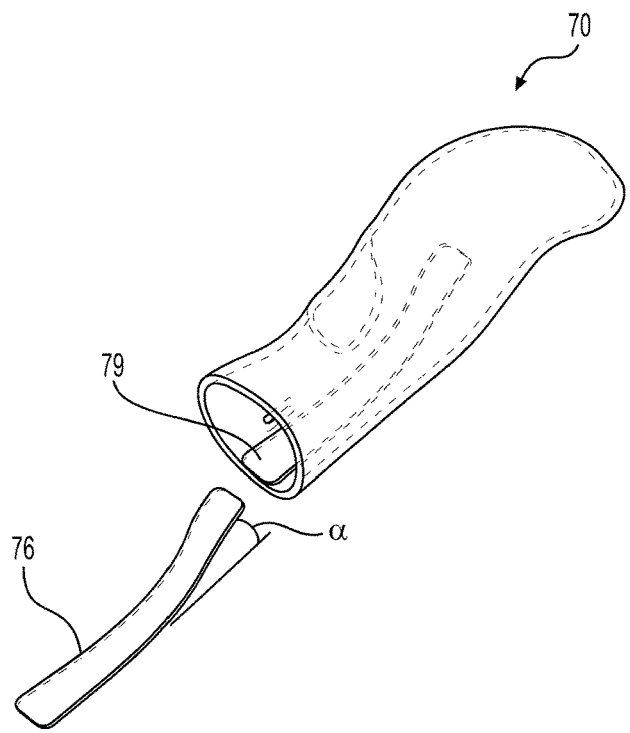
FIG. 11A is an exploded perspective view of a mitten and support plate for use with the robotic gripping assist.
Figure 11B:
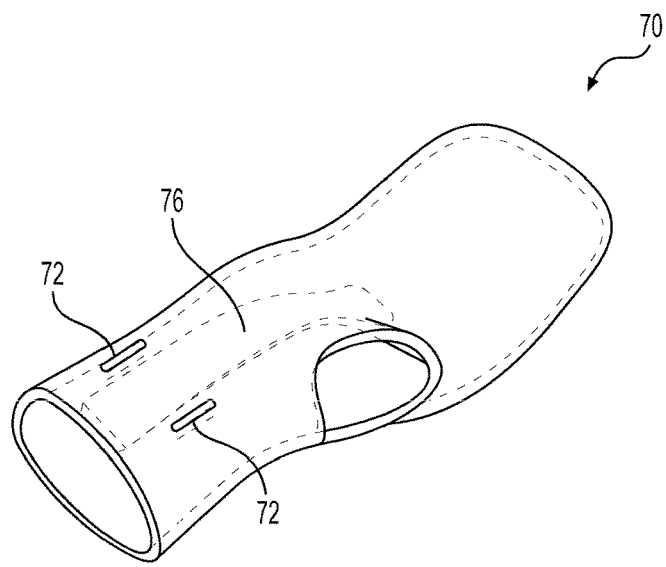
FIG. 11B is a perspective view of the mitten of FIG. 11A, shown with the support plate installed.
Figure 11C:
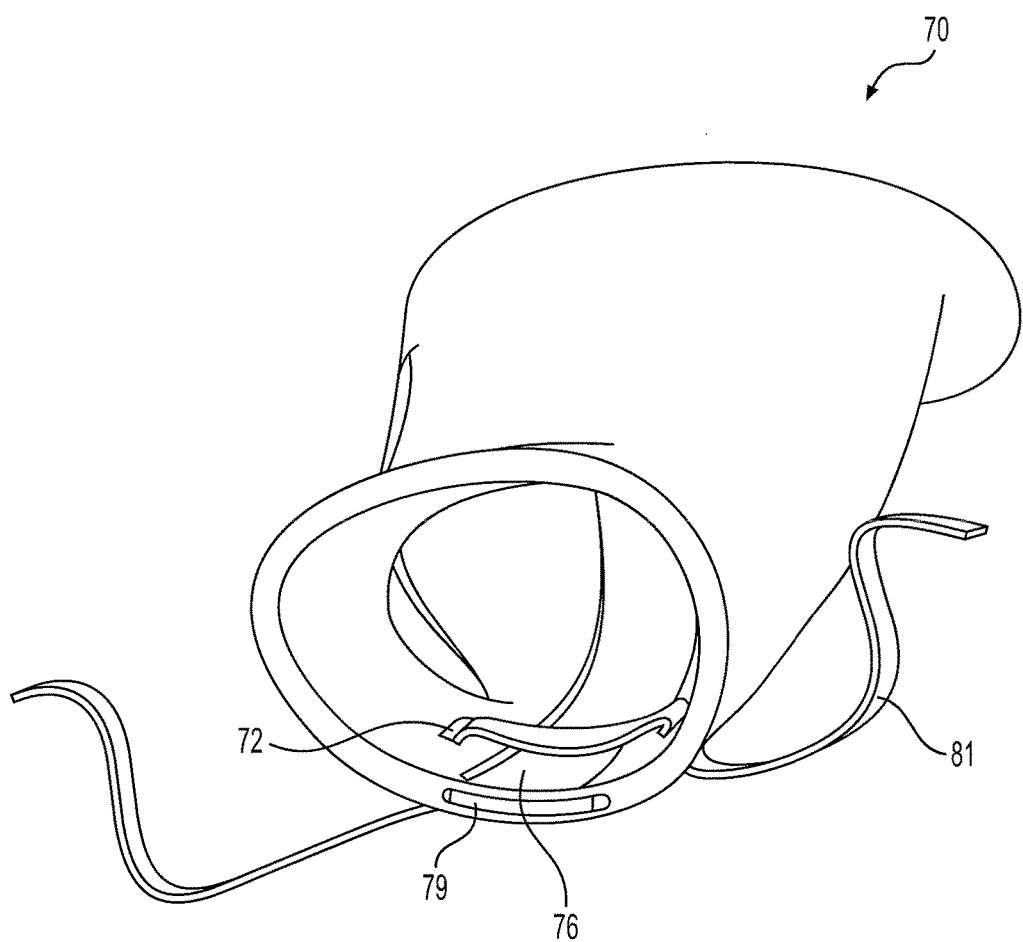
FIG. 11C is a rear perspective view of the mitten of FIG. 11A, shown with the support plate and connection strap installed.

FIGS. 11A-C show an exemplary mitten 70 that may be used with the RGA. The mitten 70 provides structure to the lower side of the user's hand and acts as an attachment medium for attaching the user's hand and arm to the RGA. The lower side of the mitten 70 includes a pocket 79 for receiving a support plate 76. The support plate 76 stabilizes the user's wrist and palm so that movements of the bending member 40 translate into curling the fingers, instead of pushing down the hand and wrist. As seen in FIG. 11A, the support plate 76 includes a substantially planar portion and an angled portion. The angled portion holds the user's wrist and palm in an upward position, and the planar portion stabilizes the support plate 76 against the user's forearm. With the palm and wrist locked in position, flexing and straightening the corrugated member 40 moves the fingers to a gripping and open position, respectively. The angle α of the angled portion may be adjusted for different hand positions to be better suited for different tasks. An increase in a will result in a raised palm, which may be more effective for griping objects in front of the user, while a decrease in a may result in a palm position better suited for overhead grabbing.

Figure 15:
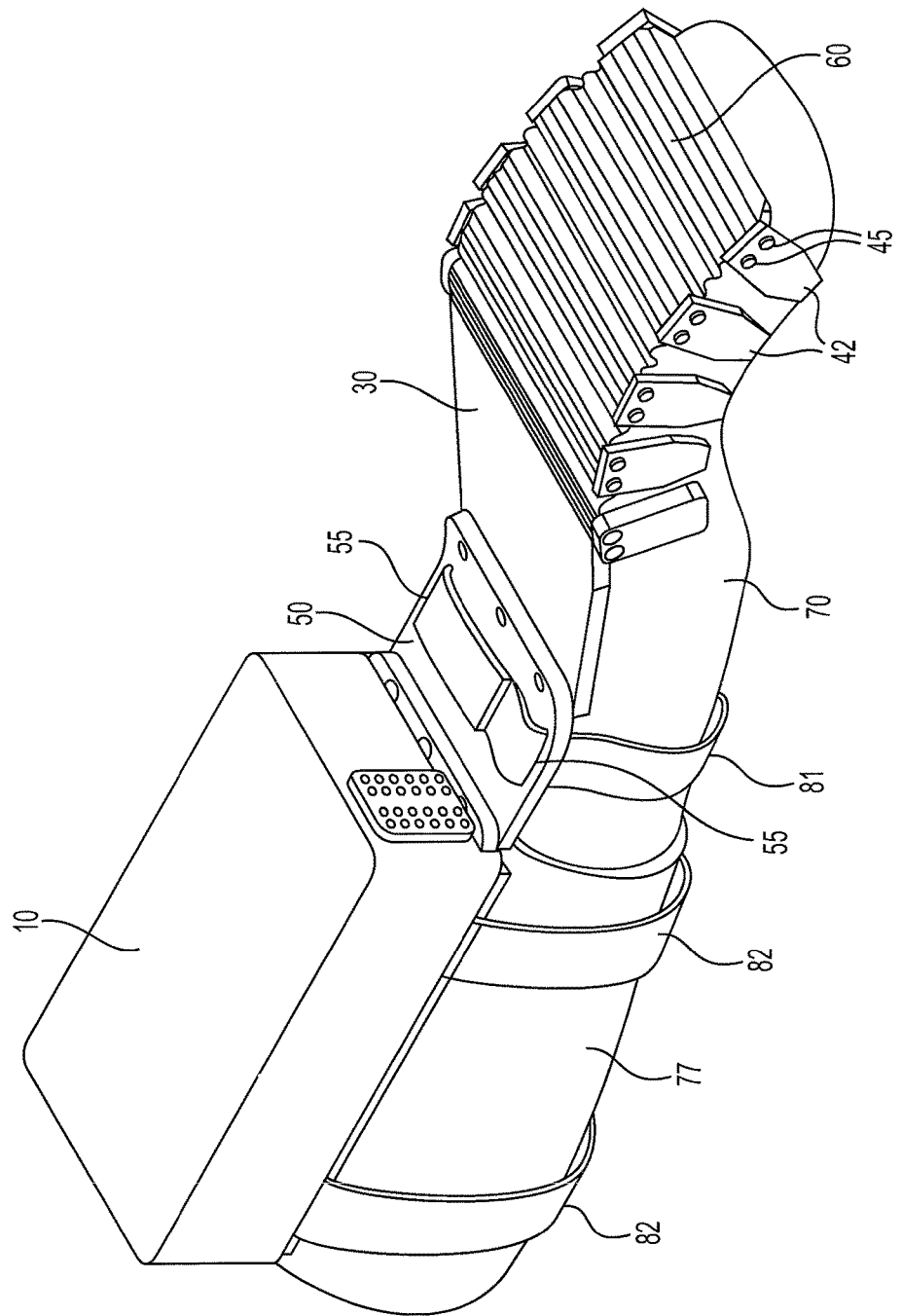
FIG. 15 is a perspective view of a robotic gripping assist, shown with the arm box and the bending member attached to the mitten and arm band, as it would be configured during use.

The mitten 70 also includes two slots 72 for receiving a connecting strap 81. When connecting the mitten 70 to the RGA, the connecting strap 81 sits above the support member 76 and extends out the two slots 72. The portion outside the slots 72 is wrapped upwards around the forearm to be threaded through slots 55 in the base member 50 for anchoring the ROS 200 to the user's arm, as seen in FIG. 15.

Figure 12A:
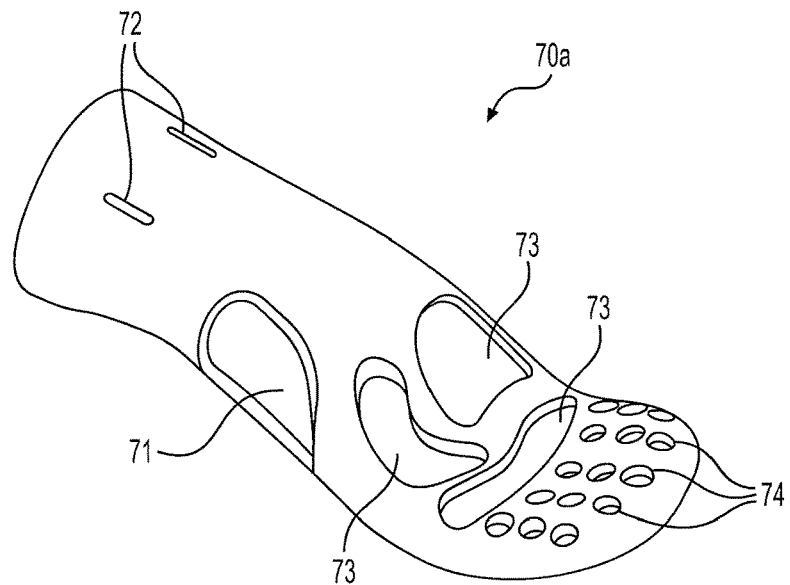
FIG. 12A is a perspective view of an embodiment of a mitten configured for providing sensory feedback.
Figure 12B:
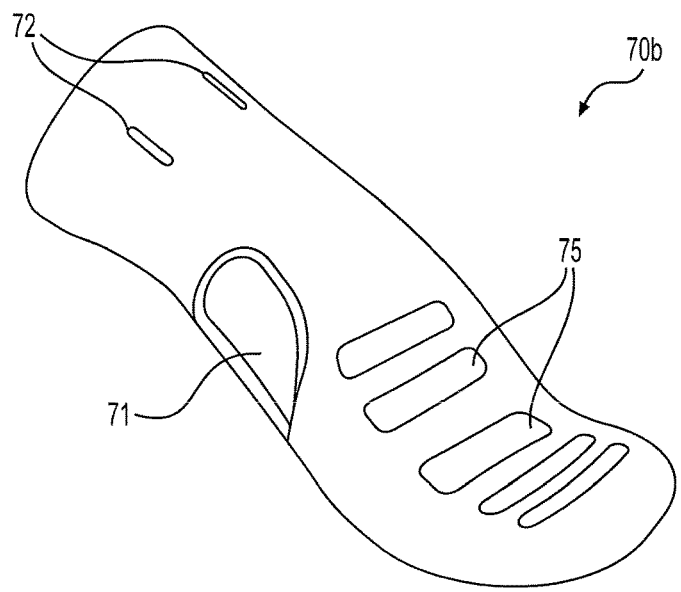
FIG. 12B is a perspective view of another embodiment of a mitten configured for providing additional grip.

FIGS. 12A-12B show two embodiments 70*a*, 70*b* of the mitten 70 that can be used with the RGA. The mitten 70*a* of FIG. 12A is designed for tasks that involve sensory feedback from the fingers/hand, as well as for tasks that benefit from the hand staying well ventilated. Accordingly, there are multiple openings 73, 74 in the palm and fingers of the mitten 70*a*. Specifically, there are multiple smaller holes 74 extending down the length of each finger, as well as multiple large holes 73 in the palm. These holes 73, 74 allow for direct contact between the user's skin and the object being touched, thus allowing the sensors in the users hand to give accurate feedback. The mitten 70*a* also defines a large hole 71 in its side for the thumb to extend out from the glove or mitten 70*a*, since the RGA is not intended to power the thumb. FIG. 12B shows an embodiment of a mitten 70*b* that is used to enhance the user's grip. The gripping strips 75 may be made of high friction materials to provide better attachment to the object being gripped. The griping strips 75 may be connected to the mitten 70*b* by hook and loop fasteners to allow for replacement when worn out, or for substitution with gripping strips 75 having different characteristics, such as texture and material. Pressure sensing pads may be integrated into the gripping strip 75 to control movement of the RGA.

Figure 13A:
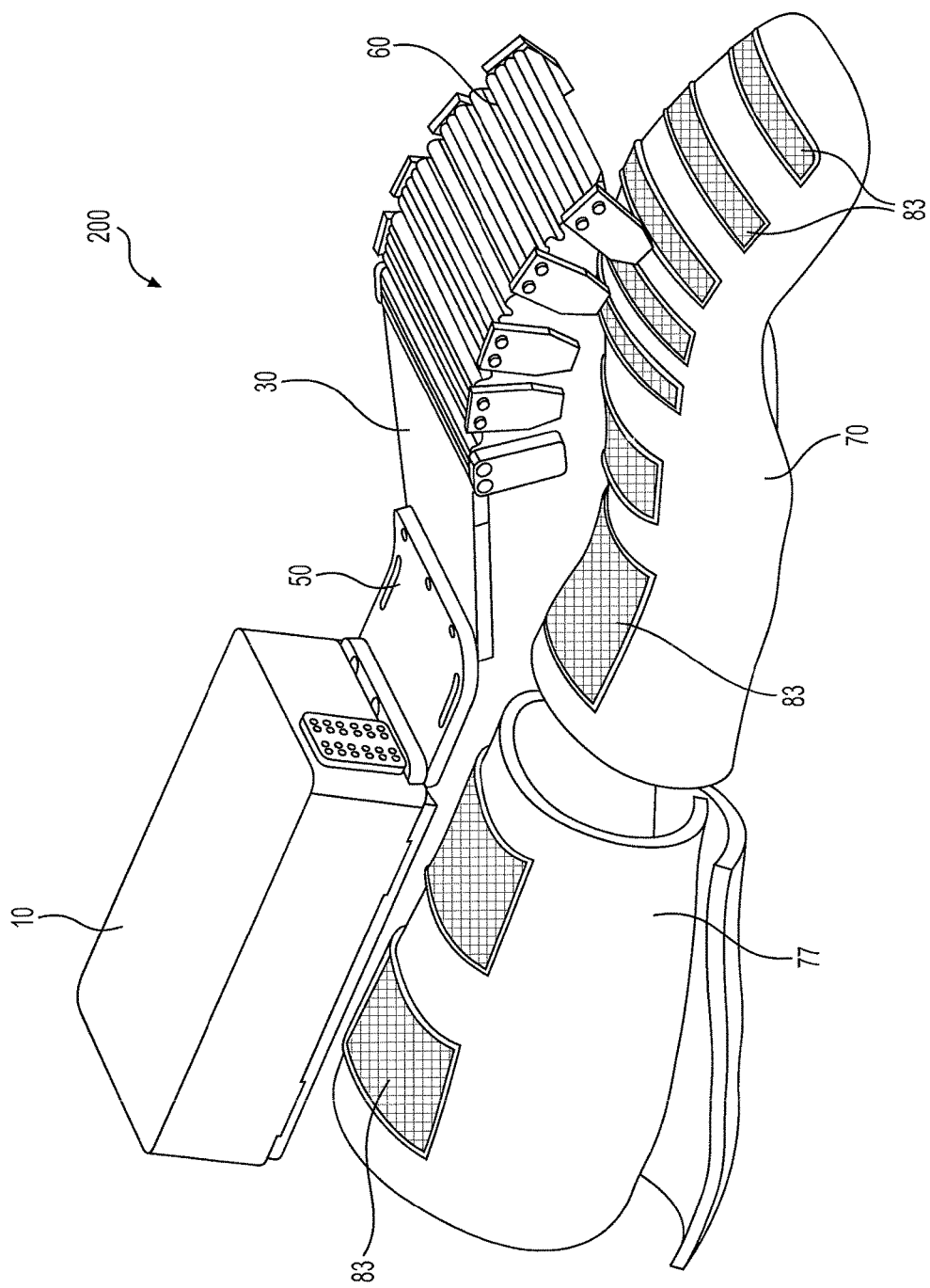
FIG. 13A is an exploded perspective view of the robotic gripping assist aligned with the mitten and arm band for attachment according to a first method of attachment to a user.
Figure 13B:
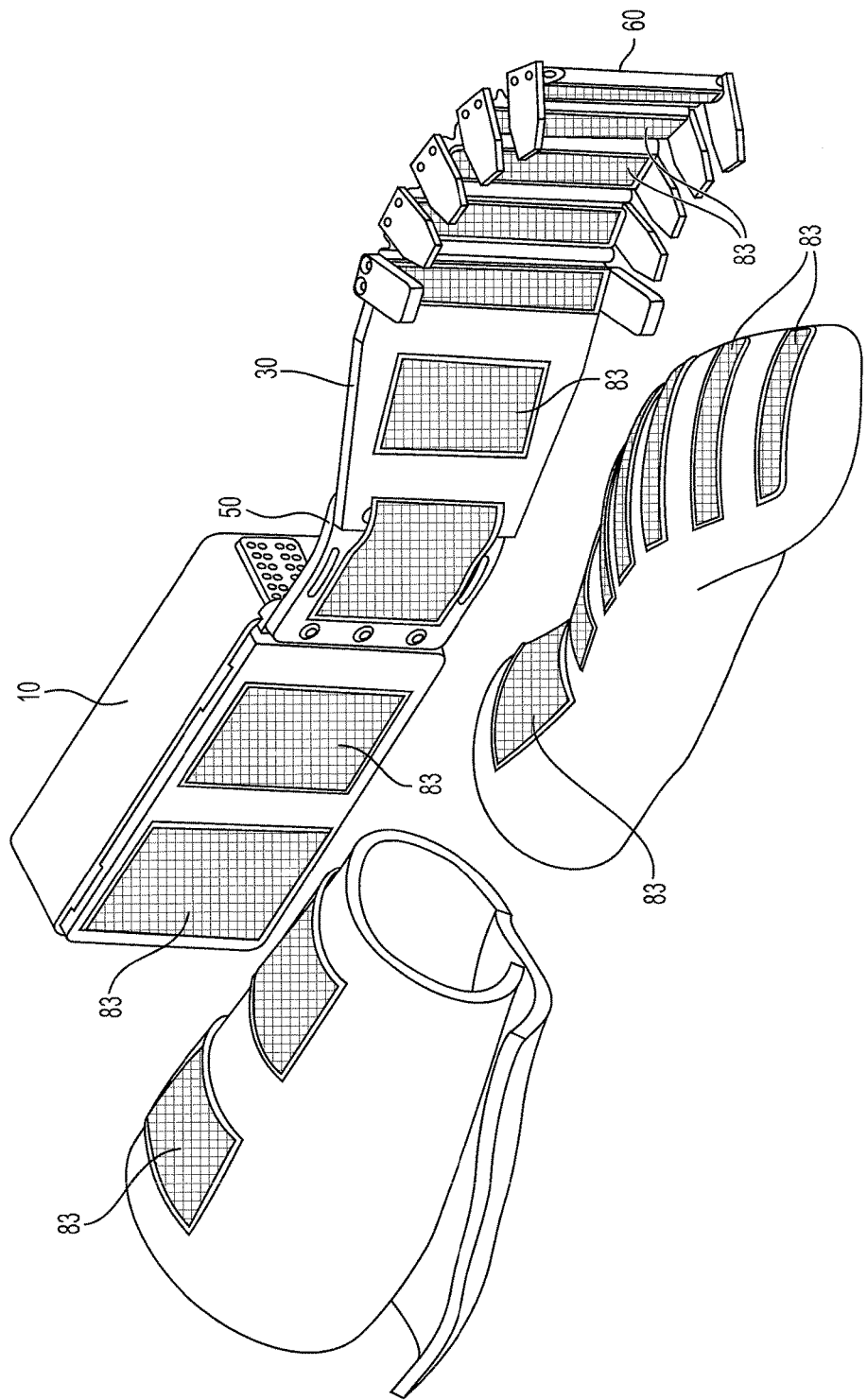
FIG. 13B is an exploded perspective view of the robotic gripping assist assembly of FIG. 13A, shown with the arm box and bending member lying on their side.

FIGS. 13A-13B show an embodiment of a mechanism for attaching the mitten 70 and an arm band or forearm sleeve 77 to the RGA 200 (wires have been removed from the RGA for clarity). The attachment mechanism includes two portions, the portion attached to the user and the portion attached to the RGA 200. In the embodiment shown in FIGS. 13A-13B, the attachment mechanism is patches of hook and loop fastening material 83. The mitten 70 and arm band 77 act as a support for attaching the hook and loop patches 83 to the user's arm. As seen in FIG. 13B, the hook and loop patches 83 on the mitten 70 have mating hook and loop patches 83 on the RGA 200. The hook and loop patches 83 on the bending member 60 are attached to the portion containing the rigid rods 41, since they will not deform during flexion. When the RGA 200 is aligned with the mitten 70 and the arm band 77, the hook and loop patches 83 will line up and create a secure connection between the user and the RGA 200.

Figure 14:
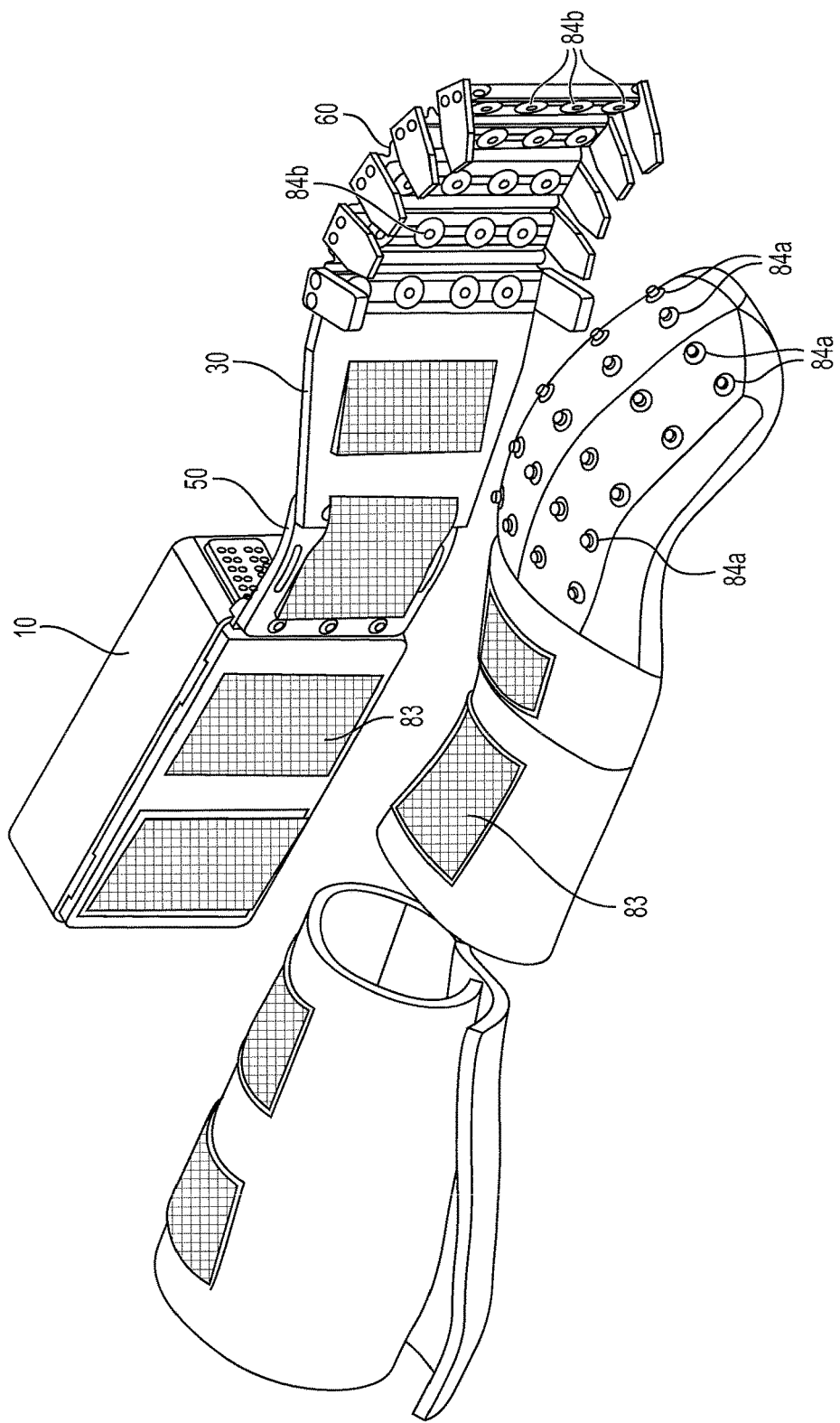
FIG. 14 is an exploded perspective view of a robotic gripping assist assembly similar to FIG. 13B but having a different method of securing the bending member to the mitten.

FIG. 14 shows an alternative embodiment of an attachment mechanism. The arm box 10, base member 50, and intermediate member 30 portions of this attachment mechanism are hook and loop patches 83, similar to the previous embodiment, and the bending member 60 is connected to the mitten 70 using snaps. As seen in FIG. 14, rows of male snaps 84a are attached to the hand portion of the mitten 70, and corresponding rows of female snap fasteners 84b are attached to the bending member 60 along the rigid rods 41. This embodiment may be used in scenarios where aligned securement between the hand and bending member 60 is critical.

FIG. 15 shown the RGA 200 fully connected to the mitten 70 and arm band 77 for use when attached to a user's arm. The top of the mitten 70 and arm band 77 are connected to the RGA using loop patches 83 and/or snap fasteners 84, as previously discussed, but cannot be seen in FIG. 15. The distal connected strap 81 extends up from the bottom of the mitten 70 and through holes in the base member 50. The two ends of the strap 81 are attached to create a tight loop around the mitten 70, the RGA 200, and the users arm within the mitten 70. The two proximal connection straps 82 each have arms that are attached at one end to the arm box 10. The arms connect to form loops for securing the arm box 10, which is the heaviest portion of the RGA 200, to the user's forearm, which is within the arm band 77.

The base member 20, intermediate member 30, and bending member 40 may each have their own stiffness characteristics that can be adjusted for user specific devices. The flexibility of the bending member 40, along with its ability to flex and extend the fingers, has already been discussed. However, the intermediate member 30 and base member 20 may also have flexibility to follow the profile of the user's hand and wrist. Typically, the bending member 40 will be the most flexible, in order to not hinder the gripping and straightening motions. The base member 20 will be the least flexible, to provide stability at the wrist, and the intermediate member will have an intermediate flexibility so that it can follow the user's hand when the wrist moves. In some cases, the individual flexibility of the bending member 40, intermediate member 30, and base member 20 may be determined based on the user's medical condition. The above flexibility pertains to all embodiments of the base member, intermediate member, and bending member.

The RGA 100 may be controlled using various methods, which may depend on the scenario or user preference. In some cases, movement of the bending member 40 may be controlled by myoelectric signals from the user. For example, a surface electromyography (EMG) sensor for indicating flexion of the fingers, moving the bending member 40 into a gripping position, may be installed on the user's flexor carpum radialis. The flexor carpum radialis is the muscle that primarily powers the gripping motion. Therefore the device will work simultaneously with the muscle based on the user's brain input. Similarly, the surface EMG sensor for indicating extension for the fingers, moving the bending member 40 to the straight position, may be placed on the ipsilateral forearm extensors, which provide power for straightening the fingers.

Alternately, operation of the RGA 100 may be controlled by pressure pads or sensors. For example, a pressure pad may be installed on the palm or fingers of the mitten 70. When the pressure pad senses a preset amount of pressure, the RGA 100 will move the bending member 40 to the gripping position for gripping an object. The object may be released by a second pressure sensor or switch that can be used for moving the bending member 40 to a straight position. Force pads or sensors may be used in place of the pressure sensors.

In cases where the user's medical condition limits use of only one hand, a remote switch or button may be used to control operation of the RGA 100. The switch/button may be held in the user's properly functioning hand, and the functioning hand can be used to operate the button, and therefore the RGA 100. This setup may be beneficial when the RGA 100 is being used as a rehabilitation tool. The above controller embodiments may be used with all embodiments of the RGA.

It is to be understood that the robotic arm assist is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A robotic gripping assist for assisting a person having a hand with weakened hand grip, comprising:
    a bending member adapted for overlying a dorsal aspect of the hand having the weakened hand grip, the bending member having opposed first and second sides;
    a first plurality of support members and a second plurality of support members, each of the support members having an upper end and a lower end, the upper ends of the first plurality of support members being connected in series along the first side of the bending member, the upper ends of the second plurality of support members being connected in series along the second side of the bending member, the lower ends of the support members being suspended below the sides of the bending member;
    a spool having first and second upper wires and first and second lower wires mounted thereon, the first lower wire being threaded through the lower end of the support members on the first side of the bending member, the second lower wire being threaded through the lower end of the support members on the second side of the bending member, the first upper wire being threaded through the upper end of the support members on the first side of the bending member, and the second upper wire being threaded through the upper end of the support members on the second side of the bending member;

a motor having a shaft; and a gear train disposed between the shaft of the motor and the spool;

wherein actuation of the motor for rotation in a first direction pulls in the lower wires and lets out the upper wires to bend the bending member downward to flex the hand having the weakened hand grip to assist gripping the object, and actuation of the motor for rotation in a second direction pulls in the upper wires and let out the lower wires to extend the hand having the weakened hand grip to assist in releasing the grip on the object.

2. The robotic gripping assist of claim 1, wherein the bending member includes rods extending between corresponding pairs of said support members on the opposing sides of the bending member, the support members being attached to the rods.

3. The robotic gripping assist of claim 2, wherein portions of the bending member between the rods define a waveform shape.

4. The robotic gripping assist of claim 3, wherein the waveform includes at least one cycle having a peak and a trough.

5. The robotic gripping assist of claim 1, further comprising an arm box supported on a forearm of the person, the arm box housing the motor and the spool.

6. The robotic gripping assist of claim 5, further comprising:

an intermediate member extending from the base member; and a base member extending from the intermediate member, the base member being attached to said arm box.

7. The robotic gripping assist of claim 5, wherein said bending member has a lower surface having a plurality of fasteners disposed thereon, the robotic gripping assist further comprising:

a mitten having an upper surface; and a plurality of fasteners disposed on the upper surface of the mitten, the fasteners on the upper surface of the mitten mating with the fasteners on the lower surface of said bending member.

8. The robotic gripping assist of claim 5, further comprising:

an intermediate member extending from the base member; and a base member extending from the intermediate member, the base member being attached to said arm box;

a mitten having an upper surface;

an arm band; and a plurality of mating fasteners attaching said arm box to the arm band and attaching said bending member to at least one of the base member, the intermediate member, and the mitten.

9. The robotic gripping assist according to claim 1, wherein the upper wires and the lower wires are wound around the spool in opposite directions.

10. The robotic gripping assist according to claim 1, wherein said bending member comprises a corrugated belt.

* * * * *